(12) United States Patent
Rousseau

(10) Patent No.: US 11,737,472 B2
(45) Date of Patent: Aug. 29, 2023

(54) LOW BULK DENSITY COMPOSITION FOR MAKING A TEA BEVERAGE HAVING REDUCED DUST OR FINES

(71) Applicant: SWM Luxembourg SARL, Contern (LU)

(72) Inventor: Cedric Rousseau, Le Mans (FR)

(73) Assignee: Mativ Holdings, Inc., Alpharetta, GA (US)

( * ) Notice: Subject to any disclaimer, the term of this patent is extended or adjusted under 35 U.S.C. 154(b) by 599 days.

(21) Appl. No.: 15/053,134

(22) Filed: Feb. 25, 2016

(65) Prior Publication Data

US 2016/0255854 A1 Sep. 8, 2016

Related U.S. Application Data

(60) Provisional application No. 62/126,891, filed on Mar. 2, 2015.

(51) Int. Cl.
*A23F 3/22* (2006.01)
*A23L 2/395* (2006.01)
(Continued)

(52) U.S. Cl.
CPC ............... *A23F 3/225* (2013.01); *A23F 3/16* (2013.01); *A23F 3/30* (2013.01); *A23F 3/34* (2013.01);
(Continued)

(58) Field of Classification Search
CPC .... A23F 3/16; A23F 3/225; A23F 3/34; A23F 3/30
See application file for complete search history.

(56) References Cited

U.S. PATENT DOCUMENTS

| 3,353,541 A | 11/1967 | Hind et al. |
| 3,386,449 A | 6/1968 | Hind |

(Continued)

FOREIGN PATENT DOCUMENTS

| CN | 1329855 A | 1/2002 |
| CN | 1565286 A | 1/2005 |

(Continued)

OTHER PUBLICATIONS

International Search Report and Written Opinion for PCT/IB2016/051044 dated Jun. 3, 2016, 10 pages.

(Continued)

*Primary Examiner* — Changqing Li
(74) *Attorney, Agent, or Firm* — Dority & Manning, P.A.

(57) ABSTRACT

The present disclosure relates to an infusion product for making a beverage, such as a tea or tea-like drink. In order to produce the composition of the present disclosure, plant materials are contacted with a solvent to remove an extract. The remaining plant materials are then formed into a fibrous structure or network, such as a sheet or fibrous layer. The extract may be further treated or concentrated and then reapplied to the plant materials. In accordance with the present disclosure, the resulting sheet or layer is then reduced to discrete pieces having a unique particle size distribution. Through the process of the present disclosure, a composition is produced that not only has a minimal amount of fines and dust, but can also have a relatively low bulk density.

19 Claims, 9 Drawing Sheets

(51) Int. Cl.

| | | |
|---|---|---|
| *A23F 3/30* | (2006.01) | |
| *A23F 3/34* | (2006.01) | |
| *A23L 2/52* | (2006.01) | |
| *A61K 8/02* | (2006.01) | |
| *A61K 8/9755* | (2017.01) | |
| *A61K 8/9789* | (2017.01) | |
| *A61K 8/9794* | (2017.01) | |
| *A23F 3/16* | (2006.01) | |
| *A23L 2/02* | (2006.01) | |

(52) U.S. Cl.
CPC .............. *A23L 2/02* (2013.01); *A23L 2/395* (2013.01); *A23L 2/52* (2013.01); *A61K 8/0208* (2013.01); *A61K 8/9755* (2017.08); *A61K 8/9789* (2017.08); *A61K 8/9794* (2017.08)

(56) References Cited

U.S. PATENT DOCUMENTS

| | | | |
|---|---|---|---|
| 3,415,253 A | 12/1968 | Michels et al. | |
| 3,420,241 A | 1/1969 | Hind et al. | |
| 3,428,053 A | 2/1969 | Schoenbaum et al. | |
| 3,467,109 A | 9/1969 | Block et al. | |
| 3,483,874 A | 12/1969 | Hind | |
| 3,561,451 A | 2/1971 | Jacin et al. | |
| 3,760,815 A | 9/1973 | Deszyck | |
| 3,860,012 A | 1/1974 | Selke | |
| 3,847,164 A | 11/1974 | Mattina et al. | |
| 4,182,349 A | 1/1980 | Selke | |
| 4,674,519 A | 6/1987 | Keritsis et al. | |
| 4,891,232 A | 1/1990 | Dahl | |
| 5,529,796 A | 6/1996 | Gobbo | |
| 5,715,844 A | 2/1998 | Young et al. | |
| 5,724,998 A | 3/1998 | Gellatly et al. | |
| 5,765,570 A | 6/1998 | Litzinger et al. | |
| 6,761,918 B2 | 7/2004 | Pulikkottil et al. | |
| 6,818,234 B1 | 11/2004 | Nair et al. | |
| 7,001,629 B1 | 2/2006 | Mengal et al. | |
| 7,793,585 B2 | 9/2010 | Ramussen | |
| 8,499,965 B2 | 8/2013 | Sheffield | |
| 8,597,667 B2 | 12/2013 | Mou et al. | |
| 8,734,881 B2 | 5/2014 | Yoakim et al. | |
| 9,220,296 B2 | 12/2015 | Fall et al. | |
| 2002/0132098 A1 | 9/2002 | Miyazawa et al. | |
| 2003/0113411 A1 | 6/2003 | Rose | |
| 2003/0187055 A1 | 10/2003 | Riker | |
| 2004/0156920 A1 | 8/2004 | Kane | |
| 2004/0180077 A1 | 9/2004 | Riker | |
| 2005/0064049 A1 | 3/2005 | Mori et al. | |
| 2005/0088632 A1 | 4/2005 | Sadi | |
| 2005/0158252 A1 | 7/2005 | Romanowski | |
| 2005/0244516 A1* | 11/2005 | Mercati ............... | A23F 3/34 424/728 |
| 2006/0165756 A1 | 7/2006 | Catani | |
| 2007/0048429 A1* | 3/2007 | Griffiths ............... | A23F 3/32 426/597 |
| 2007/0199453 A1 | 8/2007 | Ramussen | |
| 2009/0047328 A1 | 2/2009 | Cunningham | |
| 2009/0169654 A1 | 7/2009 | Banerjee | |
| 2009/0202676 A1* | 8/2009 | Colliver ............... | A23F 3/40 426/49 |
| 2010/0032444 A1 | 2/2010 | Sheffield | |
| 2010/0196545 A1 | 8/2010 | Buffet et al. | |
| 2010/0210866 A1 | 8/2010 | Toyohara et al. | |
| 2010/0233322 A1 | 9/2010 | Fukuda | |
| 2011/0020512 A1 | 1/2011 | Masutake | |
| 2011/0236502 A1 | 9/2011 | Guillory | |
| 2013/0280320 A1* | 10/2013 | Mompon ............... | A23F 3/14 424/443 |
| 2014/0224265 A1 | 8/2014 | Rouillard et al. | |
| 2014/0295049 A1* | 10/2014 | Ragot ............... | A23L 2/08 426/589 |
| 2015/0037389 A1 | 2/2015 | Ragot et al. | |
| 2015/0050371 A1 | 2/2015 | Gehling et al. | |
| 2015/0056255 A1 | 2/2015 | Ragot et al. | |
| 2015/0175810 A1 | 6/2015 | Rieland | |
| 2015/0230491 A1* | 8/2015 | Looft ............... | A23F 3/405 426/78 |
| 2015/0374624 A1 | 12/2015 | Ragot et al. | |

FOREIGN PATENT DOCUMENTS

| | | | |
|---|---|---|---|
| CN | 1957777 A | 5/2007 | |
| CN | 102919430 | 2/2012 | |
| CN | 103054156 | 4/2013 | |
| DE | 202010001912 U1 | 3/2011 | |
| JP | H 09163930 A | 6/1997 | |
| JP | H10304822 | 11/1998 | |
| JP | 2001131866 A | 5/2001 | |
| JP | 2005119967 | 5/2005 | |
| JP | 2005306742 A | 11/2005 | |
| JP | 2006000934 A | 2/2006 | |
| JP | 2006246817 A | 9/2006 | |
| JP | 2006249599 A | 9/2006 | |
| JP | 2006256968 A | 9/2006 | |
| JP | 2007098152 A | 4/2007 | |
| JP | 2008274535 A | 11/2008 | |
| JP | 2011182783 A | 9/2011 | |
| KR | 20070090286 | 9/2007 | |
| KR | 20100114348 | 10/2010 | |
| WO | WO 0205655 | 1/2002 | |
| WO | WO-2012013519 A1 * | 2/2012 | ............... A23F 3/22 |
| WO | WO-2014042235 A1 * | 3/2014 | ............... A23F 3/405 |

OTHER PUBLICATIONS

Raventos et al., Application and Possibilities of Supercritical $CO_2$ Extraction in Food Processing Industry: an Overview, Food Science Tech. Int. (2002), vol. 8 (5) pp. 269-284.
Greer, C.C,. A Text-Book of Cooking; J.S. Cushing Co.-Berwick & Smith Co. Norwood, MA 1915, pp. 175-177.
Innovation Food Online, Sodium Alginate; URL<https://innovationinfood.wikispaces.com/Sodium+alginate> Published Jan. 4, 2007 Online, 7 pages with one extra page having google search hit with datestamp.
CN20090097787; Huimin, Y., dated Apr. 2009, English Abstract Only, 2 pages.
SU1181061; Choladze, et al., dated Jun. 1985,English Abstract Only, 2 pages.
Blumenthal et al., Herbal Medicine, Expanded Commission E. Monographs, 2000, pp. 393-400.
Adams et al., Analysis of the Interactions of Botanical Extract Combinations Against the Viability of Prostate Cancer Cell Lines, Mar. 2003, pp. 117-124.
Lin et al., Inhibition of Helicobacter Pylori and Associated Urease by Oregano and Cranberry Phytochemical Synergies, Applied and Environmental Microbiology, Dec. 2005, vol. 71., No. 12, pp. 8558-8564.
Co-pending U.S. Appl. No. 15/506,620, filed Feb. 24, 2017.

* cited by examiner

LOW BULK DENSITY COMPOSITION FOR MAKING A TEA BEVERAGE HAVING REDUCED DUST OR FINES

RELATED APPLICATIONS

The present application is based on and claims priority to U.S. Provisional Patent Application Ser. No. 62/126,891, filed on Mar. 2, 2015, which is incorporated herein by reference.

FIELD

The present invention relates to an infusion product for making a beverage, more specifically to a plant-based composition for making a beverage, and to a herbal and/or vegetable composition or bouquet garni, for food, medicinal or aromatic applications. The plants (raw materials) are fruits, herbs, medicinal plants, tea, vegetables and/or spices.

BACKGROUND

A quick cup of tea, either from herbs, medicinal plants or tea plants (*Camellia sinensis*), also called "infusion" or "tisane" may be produced by putting conventional tea bags filled with parts of the fruits, herbs, medicinal plants, or tea (such as, for example, in the form of leaves or powder) in a cup of hot or boiling water. For some teas, such as fruit teas or teas made from herbs or medicinal plants, the steep time is rather long, whereas for various kinds of tea plants, maintaining a certain steep time is required for producing the best flavour. In some cases, there is either an incomplete extraction from the bag, resulting in a highly variable and generally weak flavored beverage, or an excessive extraction, resulting in a highly variable and generally strong or even bitter taste. The flavour and taste also greatly depends on water quality and temperature.

In order to increase the amount of flavor while decreasing the steep time of teas, the tea leaves that are used to produce a tea blend or an herbal tea blend are ground or shredded to a relatively small size. By grinding or shredding the plant matter into small sizes, greater surface area is produced that should decrease the amount of time it takes for the material to wet when contacted with water and should allow greater amounts of the plant extract to infuse into the water. Unfortunately, grinding or shredding the plant material into small sizes can produce a number of problems and drawbacks.

For instance, grinding or shredding the plant material produces dust and fines. The dust and fines make it harder to process the plant material and to fill the plant material into tea bags.

In addition, the dust and fines that are produced when creating a tea blend or herbal tea blend can escape through many tea bag materials and create unwanted residue when the tea bag is later immersed in water. Consequently, many tea bags are made from highly engineered porous materials that can significantly increase the cost of the product. Lowering the pore size of the tea bag material also has a tendency to increase the steep time of the tea.

The presence of dust and fines in tea blends is also not desirable from a consumer standpoint. The presence of dust and fines, for instance, can lower the aesthetics of the product and can make many tea bags look empty as if the tea bag does not contain a full dose of the tea blend. In particular, the presence of dust and fines can significantly increase the bulk density of the blend material which reduces the filling power of the tea blend when placed in a tea bag.

In view of the above, a need exists for improved infusion products for making tea beverages. In particular, a need exists for a composition for producing a tea or tea-like beverage that can reduce fines and dust without decreasing flavor or increasing steep time. A need also exists for a composition for producing a tea beverage or a tea-like beverage that has greater filling power than many conventional tea blends.

SUMMARY

In one embodiment of the present disclosure, a composition for making a beverage is provided, the composition comprising a fibrous structured matrix material, such as a layer or sheet, of a reconstituted plant product and a plant extract applied thereto. In accordance with the present disclosure, in one embodiment, the structured matrix material formed from the fibrous plant material and plant extract is reduced in size without creating substantial amounts of fines or dust. The structured matrix material of fibrous plant material, for instance, can be ground, shredded, cut, stamped, slit, or the like. In one embodiment, the fibrous structured matrix material may comprise an extruded structure that has been treated with a plant extract. When producing the structured matrix material through extrusion, the product may not need to be reduced in size when later used. For instance, in one embodiment, the extruded structure may be in the form of pellets. Of particular advantage, the structured matrix material of fibrous plant product treated with the plant extract has been found to have higher infusion yield and infusion speed. Consequently, the sheet can be reduced to pieces having larger sizes in comparison to many tea blends in the past without increasing steep time. Consequently, a tea blend or herbal tea blend can be produced according to the present disclosure that not only has reduced fines and dust, has a decreased steep time, but also can have a lower bulk density that increases the filling power of the composition. In addition, because the composition of the present disclosure produces less dust and fines when used in a tea bag product, the tea bag can be made from a more porous and possibly less expensive material that can further decrease steep time.

In one embodiment, for instance, the present disclosure is directed to a composition for producing a beverage or broth by soaking the composition in a liquid. The composition comprises a structured matrix material, such as a sheet, formed from plant materials that have been treated with a plant extract. The plant material used to form the composition can comprise any suitable plant as will be described in greater detail below. In one embodiment, for instance, the plant material comprises materials obtained from a tea plant, an herbal tea plant, a fruit, a vegetable, a spice, or mixtures thereof. The composition is in the form of discrete pieces. The pieces have a particle size distribution such that when the composition is subjected to a sieve test using a RETSCH sieve shaker AS200, less than about 25% of the pieces pass through a sieve having a square mesh size of 1 mm. For instance, less than about 20%, such as less than about 15%, such as less than about 10%, such as less than about 8%, such as less than about 6%, such as even less than about 5% of the pieces pass through a sieve having a square mesh size of 1 mm.

In addition, the composition can be prepared such that greater than about 5% of the discrete pieces fail to pass through a sieve having a square mesh size of 2 mm. For instance, the composition can be prepared so that greater than about 7%, such as greater than about 10%, such as greater than about 13%, such as greater than about 15%, such as greater than about 17%, such as greater than about 20%, such as greater than about 25%, such as greater than about 30%, such as greater than about 35%, such as greater than about 40%, such as greater than about 45%, such as greater than about 50%, such as greater than about 55%, such as greater than about 60%, such as greater than about 70%, such as even greater than about 80% of the pieces fail to pass through a sieve having a square mesh size of 2 mm. The sieve test is described in greater detail below.

As described above, the reconstituted structured matrix material formed from plant materials that has been treated with a plant extract can be formed from many different types of plants. The plant can be, for example, selected from the group consisting of fruits, herbs, medicinal plants, tea, vegetables and spices, including mixtures thereof, such as, for example, mixtures of herbs, vegetables and/or spices. In one embodiment, the composition is for producing a tea or tea-like beverage (including herbal tea beverages). In this regard, the structured matrix material can be formed from plant materials comprising a white tea blend, a yellow tea blend, a green tea blend, a black tea blend, an oolong tea blend, a pu-erh tea blend, a rooibos tea blend, and the like. The composition can be made exclusively from the structured matrix material formed from plant materials that has been treated with a plant extract or can comprise discrete pieces of the sheet blended with a natural tea blend or herbal tea blend. For instance, in one embodiment, from about 1% to about 98% of the pieces contained in the composition are produced from the sheet formed from the plant materials.

The composition of the present disclosure in addition to having virtually no fines or dust can also have a relatively low bulk density. For instance, the bulk density can be less than about 0.2 g/cm$^3$. More particularly, the bulk density can be less than about 0.15 g/cm$^3$, such as less than about 0.1 g/cm$^3$, such as less than about 0.08 g/cm$^3$, such as even less than about 0.06 g/cm$^3$. By having a relatively low bulk density, the composition has increased filling power meaning that relatively small amounts of weight of the composition can take up a significant volume, such as a significant volume of a tea bag.

The structured matrix material formed from the plant materials may comprise a blend of different plants or may be formed from a single type of plant. The reconstituted structured matrix material can be formed from leaves, stems, bark, or any other suitable part of the plant. In one embodiment, the structured matrix material formed from the plant materials and the plant extract applied to the structured matrix are obtained from at least one common plant. When producing a tea beverage, at least about 70% by weight of the plant material and at least about 70% by weight of the plant extract are obtained from one or more tea plants or from one or more herbal tea plants.

In addition to a composition, the present disclosure is also directed to a method of producing the composition and directed to a tea or herbal tea product. The tea or herbal tea product may comprise a liquid porous pouch containing the composition as described above.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
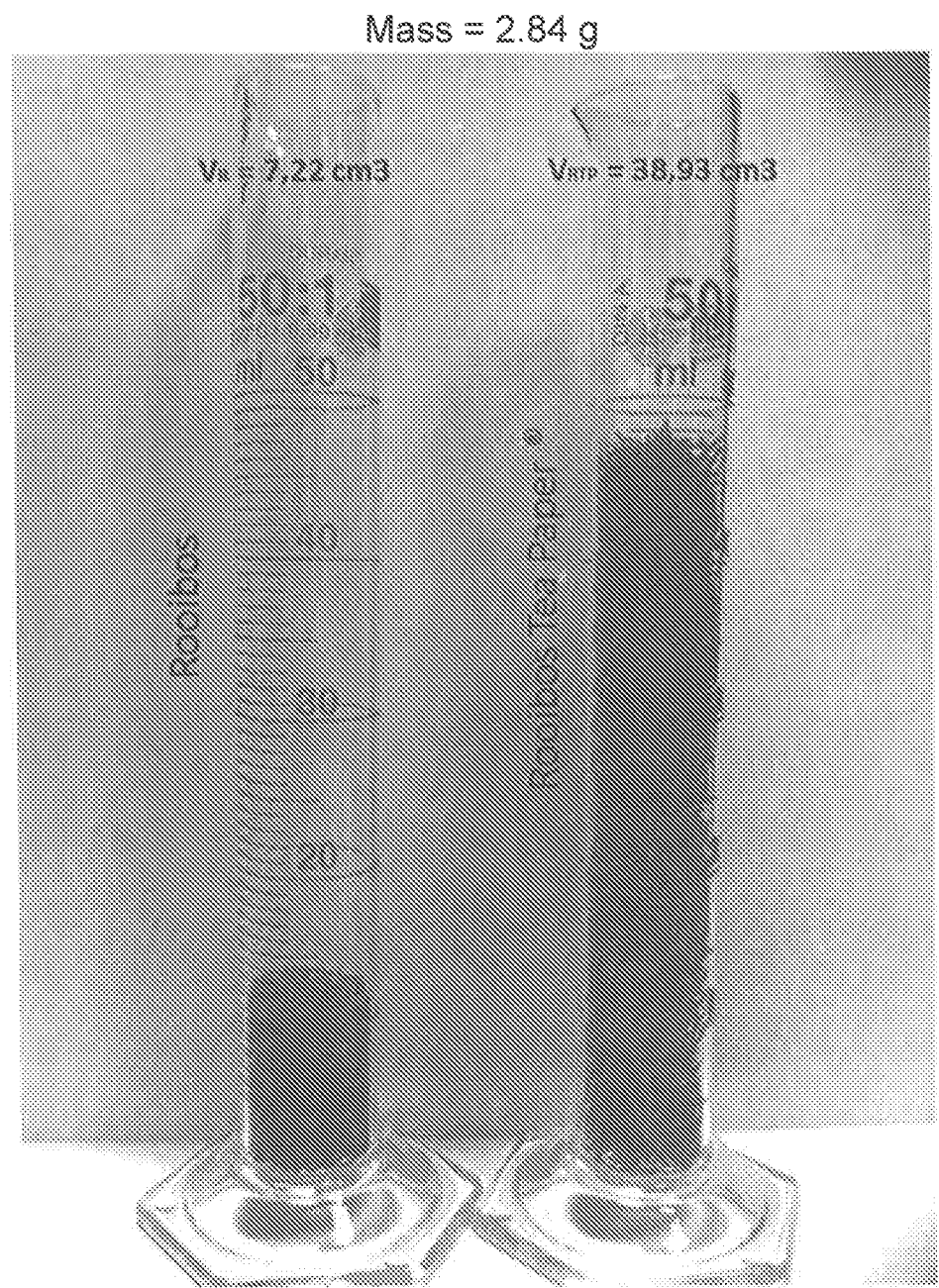
FIGS. 1-6 illustrate the results obtained in the examples below.

Repeat use of reference characters in the present specification and drawings is intended to represent the same or analogous features or elements of the present invention.

DETAILED DESCRIPTION

It is to be understood by one of ordinary skill in the art that the present discussion is a description of exemplary embodiments only, and is not intended as limiting the broader aspects of the present disclosure.

In one embodiment, a composition for making a beverage (such as a drink) is provided, the composition comprising a reconstituted fibrous plant product and a plant extract applied thereto. As used herein, a reconstituted structured matrix material refers to a fibrous structure formed from plant materials that have been contacted with at least one solvent and then formed into a fibrous network and is differentiated from a simple mixture of plant materials, whether dried or oxidized. In accordance with the present disclosure, the fibrous structured matrix material treated with a plant extract may be reduced into discrete pieces. The pieces can have any suitable size and shape and, in one embodiment, may have a size that generally mimics the size of tea leaves or leaf fragments. No matter the manner in which the structured matrix material is reduced into the discrete pieces and no matter the ultimate shape of the discrete pieces, in accordance with the present disclosure, a composition can be produced that has a minimal amount of dust and fines. In fact, in one embodiment, the resulting composition may contain virtually no dust or fines. When used to produce a beverage, such as a tea or tea-like beverage, or when used to produce a broth, the composition of the present disclosure provides various advantages and benefits.

For instance, the composition of the present disclosure has a unique overall particle size distribution in relation to conventional tea blends and herbal tea blends. The particle size distribution in conjunction with relatively low amounts of fines and dust improves blend volume and limits the loss of particles from a tea bag when soaked in water. The composition of the present disclosure has excellent filling power due to its relatively low bulk density. In this manner, when the composition is loaded into a tea bag, the composition occupies a greater volume of the tea bag in comparison to a conventional tea blend at the same loading weight. Thus, when loaded into a tea bag, the composition creates the impression that greater amounts of the material are present. In addition, the relatively low bulk density of the composition is coupled with improved infusion kinetics. Specifically, the composition of the present disclosure, in some embodiments, can show a significant improvement in tea infusion level and speed in relation to conventional tea blends.

The minimal amount of fines and dust present in the composition can also provide other improvements when designing a product that is intended to be soaked in a liquid for producing a beverage or broth. For instance, the pouch or tea bag in which the composition is placed can have a relatively high pore size without the fear of small particles forming sediment or residue in the beverage or broth that is being produced. When producing a tea beverage or a tea-like beverage, for instance, less sophisticated and less expensive bag materials may be used to produce the tea bags. For instance, in one embodiment, high porosity papers may be used as the tea bag. In an alternative embodiment, a polyamide polymer, such as nylon, may be used to produce the tea bag which can significantly reduce the cost of the product. Of particular advantage, less expensive materials may be used to design a pouch or tea bag without affecting infusion rates. In fact, due to the manner in which the composition of the present disclosure is made, infusion rates can actually increase in addition to infusion levels.

As described above, the composition of the present disclosure is formed from a fibrous plant structured matrix material that has been treated with a plant extract. The fibrous plant structured matrix material may comprise a layer or sheet or may comprise an extruded structure. In order to form the structured matrix material, plant materials, which can include leaves, dust, fannings, stems, bark, roots, and any other plant matter, are reduced to a desired particle size and combined with water to remove a diluted extract. The undissolved solids are fed through a process, similar to a papermaking process, and formed into a sheet or extruded into any suitable shape. The soluble portion, on the other hand, can be concentrated and then reapplied to the undissolved portion.

The resulting structured matrix material as described above may be referred to as a reconstituted material made from plant materials. In accordance with the present disclosure, the plant used to form the sheet may comprise fruits, herbs, medicinal plants, tea, vegetables, and/or spices, including mixtures thereof. For instance, herbs can be combined with vegetables or herbs can be combined with spices. In other embodiments, tea leaves can be combined with any suitable flavoring, spice or herb.

The structured matrix material made from plant materials that has been treated with an extract can then be further prepared in all shapes, dimensions and formats. For instance, the structured matrix material, such as a sheet, can be reduced into discrete pieces through any suitable process. The sheet, for instance, can be ground, shredded, cut, stamped, slit, extruded or the like. The resulting pieces can have any suitable shape such as disks, squares, strands, or irregular shaped flakes. In one embodiment, the sheet can be cut or stamped to form discrete pieces having a unique shape. The pieces, for instance, may have a shape and/or texture to appear as leaves or any other suitable figure. For instance, in an alternative embodiment, the sheet can be cut or stamped into fanciful or decorative shapes, such as the shape of a teacup or teapot. In an alternative embodiment, the sheet of plant material can be reduced into discrete pieces that look similar to pieces contained in a natural tea blend, except without the presence of significant amounts of dust and fines. In still another embodiment, the sheet of fibrous material can be reduced or extruded into discrete pieces that resemble round pellets, in order to mimic gunpowder tea.

Figure 8:
FIG. 8 is a perspective view of another embodiment of a composition made in accordance with the present disclosure.
Figure 9:
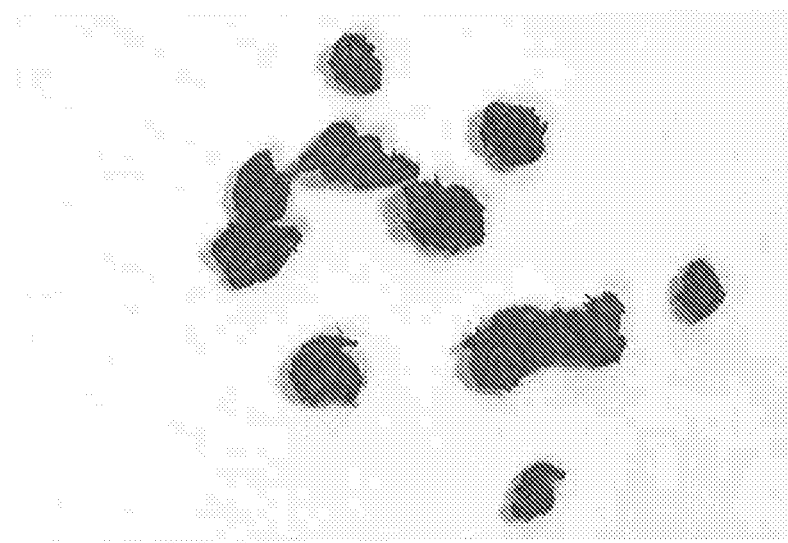
FIG. 9 is a perspective view of yet another embodiment of a composition made in accordance with the present disclosure.
Figure 10:
FIG. 10 is a perspective view of yet another embodiment of a composition made in accordance with the present disclosure.
Figure 11:
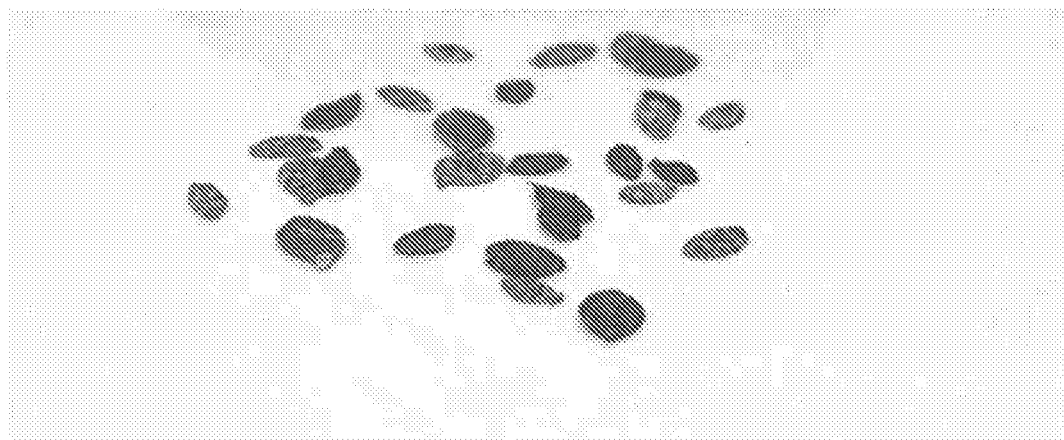
FIG. 11 is a perspective view of another embodiment of a composition made in accordance with the present disclosure.

Referring now to FIGS. 7-11, various different compositions made in accordance with the present disclosure are shown in which the discrete pieces have different shapes. For instance, in FIG. 7, the composition of the present disclosure is shown in the form of strands. In FIG. 8, the discrete pieces have a disk-like shape. In FIG. 9, the discrete pieces are in the form of small round pellets. In FIGS. 10 and 11, on the other hand, a layer or sheet of fibrous material has been cut into the shape of leaves or the fibrous plant material has been molded into the illustrated shapes. The leaves can all generally look the same or have different sizes. In addition, it should be understood that the different shapes can be combined together to produce the composition. For instance, the strands illustrated in FIG. 7 may be combined with the leaves shown in FIG. 10 or 11.

Ultimately, a composition can be formed that has relatively large pieces that would be appealing to a consumer. Larger pieces, such as those in the shapes of leaves, are usually associated with higher quality tea products.

Once the structured matrix material of plant material is optionally reduced into discrete pieces, the pieces can be used to produce a beverage or broth. In one embodiment, the discrete pieces can be used to replace a portion of a natural tea blend. For instance, the composition of the present disclosure can be combined with a natural tea blend to produce a resulting product. The resulting product may contain the composition of the present disclosure in an amount greater than about 1% by weight, such as in an amount greater than about 10% by weight, such as in an amount greater than about 20% by weight, such as in an amount greater than about 30% by weight, such as in an amount greater than about 40% by weight, such as in an amount greater than about 50% by weight, such as in an amount greater than about 60% by weight, such as in an amount greater than about 70% by weight, such as in an amount greater than about 80% by weight, such as in an amount greater than about 90% by weight. The resulting product generally contains the composition of the present disclosure in an amount from 100% by weight to less than about 90% by weight, such as less than about 80% by weight, such as less than about 70% by weight, such as less than about 60% by weight.

In an alternative embodiment, the composition may be used alone to produce a beverage or broth without being combined with any other materials.

The use of the reconstituted structured matrix material made from plant materials treated with an extract provides various improvements and advantages in addition to reducing fines and dust. For instance, due to the manner in which the fibrous structure of plant material is produced, various different qualities and characteristics of the sheet can be controlled. For instance, the chemical constitution of the composition, the consistency of the structured matrix, the sensory profile of the structured matrix, and the physical characteristics of the structured matrix can be controlled by changing the manner in which the plant material is formed into the structured matrix and by changing the chemical composition of the extract that is applied to the structured matrix. In addition, the structured matrix material of plant matter made in accordance with the present disclosure has been found to have higher infusion kinetics and a more complete infusion of the flavors than conventional tea materials. In addition, not only can undesirable components be removed from the extractant prior to reapplying the extractant to the plant material, but other ingredients can be added to the structured matrix material such as flavors or sweeteners.

As described above, the fibrous structured matrix material of the present disclosure formed from plant materials and treated with a plant extract can be reduced to discrete pieces having a unique size distribution. A size distribution can be selected that minimizes the inclusion of dust or fines, that decreases bulk density, and that provides a composition that is well suited for producing a beverage or broth when contacted with a liquid such as water.

As used herein, the particle size distribution of the composition is determined using a sieve test. In accordance with the present disclosure, sieving is carried out in a RETSCH sieve shaker AS200 with seven sieves having square mesh sizes of 4 mm, 3.15 mm, 2 mm, 1 mm, 0.5 mm, and 0.16 mm. In order to conduct a sieve test in accordance with the present disclosure, the following procedure is followed:

1. A sample of the material to be analyzed is weighed and the weight amount is recorded. The amount of sample tested can be from 3 grams to 10 grams.

2. The sample to be analyzed is deposited on the top of the sieve assembly. The sieve assembly includes a decreasing order of mesh sizes starting at the 4 mm mesh on the top and ending at the 0.16 mm mesh at the bottom using the sieve sizes described above.

3. After the sample is placed on the 4 mm mesh size screen, the cover is secured to the first sieve.

4. The sieves are then vibrated with an amplitude of 55 as indicated on the RETSCH sieve shaker AS200 for one minute.

5. After one minute, the sieve assembly is disassembled. The amount of material on each sieve is then weighed and the weight is recorded.

6. The weight of the material recovered in each sieve is then calculated as a percentage of the total weight of the initial sample.

7. The above procedure is repeated three times and the results are averaged.

Compositions made in accordance with the present disclosure can have a particle size distribution such that many of the discrete pieces have at least one dimension greater than 1 mm and wherein the composition contains little to no fines or dust. For instance, the composition of the present disclosure can have a particle size distribution such that less than about 1% of the pieces pass through a sieve having a square mesh size of 0.5 mm. More particularly, the composition can have a particle size distribution such that less than about 0.8%, such as less than about 0.5%, such as less than about 0.3% of the pieces pass through a sieve having a square mesh size of 0.5 mm. In one particular embodiment, the composition contains virtually no pieces that pass through a sieve having a square mesh size of 0.5 mm.

In one embodiment, the composition can be formulated such that less than about 25% of the pieces pass through a sieve having a square mesh size of 1 mm. More particularly, the composition can have a particle size distribution such that less than about 20%, such as less than about 18%, such as less than about 15%, such as less than about 13%, such as less than about 10%, such as less than about 9%, such as less than about 8%, such as less than about 7%, such as less than about 6%, such as less than about 5%, such as less than about 4%, such as less than about 3% of the pieces pass through a sieve having a square mesh size of 1 mm.

As described above, in addition to having a relatively small proportion of small pieces, the composition can have a relatively large proportion of pieces having at least one dimension greater than 1 mm, such as greater than about 1.5 mm, such as greater than about 2 mm, such as greater than about 2.5 mm, such as greater than about 3 mm, such as greater than about 3.5 mm, such as greater than about 4 mm, such as greater than about 4.5 mm, such as greater than about 5 mm. For example, the composition can be prepared such that greater than about 5% of the pieces fail to pass through a sieve having a square mesh size of 2 mm. Particularly, the composition can contain discrete pieces such that greater than about 7%, such as greater than about 10%, such as greater than about 12%, such as greater than about 15%, such as greater than about 17%, such as greater than about 20%, such as greater than about 22%, such as greater than about 25%, such as greater than about 27%, such as greater than about 30%, such as greater than about 32%, such as greater than about 35%, such as greater than about 37%, such as greater than about 40%, such as greater than about 42%, such as greater than about 45%, such as greater than about 47%, such as greater than about 50%, such as greater than about 52%, such as greater than about 55%, such as greater than about 57%, such as greater than about 60%, such as greater than about 62%, such as greater than about 65%, such as greater than about 67%, such as greater than about 70%, such as greater than about 72%, such as greater than about 75%, such as greater than about 77%, such as greater than about 80%, such as greater than about 82%, such as greater than about 85%, such as greater than about 87%, such as greater than about 90%, such as even greater than about 95% of the pieces fail to pass through a sieve having a square mesh size of 2 mm. In one embodiment, 100% of the pieces may fail to pass through a sieve having a square mesh size of 2 mm.

The particle size distribution of the composition of the present disclosure can be controlled by controlling the manner in which the structured matrix material of fibrous plant material treated with the extract is reduced to discrete pieces. In one particular embodiment, the sheet of fibrous plant material can be shredded so as to produce a composition containing strands wherein the strands generally have a largest dimension of from about 2 mm to about 10 mm. In an alternative embodiment, the sheet of fibrous plant material can be stamped or otherwise cut into discrete pieces having a unique shape or figure. In another embodiment, the discrete pieces can be formed through a molding process or an extrusion process where a further reduction in size is not needed. For instance, the pieces may resemble leaves. In this embodiment, more than 50% of the pieces may have a length greater than about 1 mm, such as greater than about 1.5 mm, such as greater than about 2 mm, and generally less than about 10 mm, such as less than about 8 mm, such as less than about 6 mm, such as less than about 5 mm. The width of the pieces can generally be greater than about 1 mm, such as greater than about 2 mm, but less than about 6 mm, such as less than about 5 mm, such as less than about 4 mm, such as less than about 3 mm.

In addition to having a unique particle size distribution, the composition of the present disclosure also has a relatively low bulk density. By having a low bulk density, the composition has greater filling power meaning that the composition occupies greater volume at less weight. In one embodiment, for instance, the composition can have a bulk density of less than about 0.2 $g/cm^3$. For instance, the composition can have a bulk density of less than about 0.18 $g/cm^3$, such as less than about 0.15 $g/cm^3$, such as less than about 0.13 $g/cm^3$, such as less than about 0.1 $g/cm^3$, such as less than about 0.08 $g/cm^3$, such as even less than about 0.05 $g/cm^3$. The bulk density is generally greater than about 0.005 $g/cm^3$.

The composition of the present disclosure can be produced from plant matter obtained from one or more plants.

As used herein, the term "plant" refers to any living organism of the kingdom Plantae and includes plants described as grains, fruits and vegetables as well as plant parts, such as roots, barks, seeds, stems, leaves, flowers and fruits.

The plant can be, for example, selected from the group consisting of fruits, herbs, medicinal plants, tea, vegetables and/or spices, including mixtures thereof, such as mixtures of herbs and vegetables, or herbs and spices.

As used herein, a spice is a dried seed, fruit, root, bark, or vegetative substance primarily used for flavoring, coloring or preserving food. As used herein, herbs are any plants used for flavoring, food, medicine, or perfume. Culinary use typically distinguishes herbs as referring to the leafy green parts of a plant (either fresh or dried), from a "spice", a product from another part of the plant (usually dried), including seeds, berries, bark, roots and fruits.

The fruits, herbs, medicinal plants, tea, vegetables and spices can be, for example, selected from artemisia, balm, basil, chamomile, chive, cloves, coffee, coriander, dill, garlic, ginger, *ginseng, gingko*, jasmine, lavender, mint, orange blossom, oregano, persil, rooibos, *rosa centifolia*, rosemary, thyme, turmeric, sage, pepper, chili pepper, *stevia rebaudiana*, tarragon, white tea, yellow tea, green tea, oolong tea, black tea, pu-erh tea, *vanilla*, red or green vine, violet and/or willow.

The plant can be selected from the group consisting of teas and herbal teas such as:

Anise tea (seeds or leaves), Asiatic penny-wort leaf, Artichoke tea, Bee Balm, Boldo, Burdock, Caraway tea, Catnip tea, Chamomile tea, Che Dang tea (*Ilex causue* leaves), Chinese knot-weed tea, *Chrysanthemum* tea, Cinnamon, Coca tea, Coffee tea leaves and coffee cherry tea, Cerasse, Citrus peel (including bergamot, lemon and orange peel), Dandelion coffee, Dill tea, *Echinacea* tea, Elderberry, European Mistletoe (*Viscum album*), Essiac tea, Fennel, Gentian, Ginger root, *Ginseng*, Goji, Hawthorn, Hibiscus, Ho Yan Hor Herbal Tea, Honeybush, Horehound, Houttuynia, *Hydrangea* tea (*Hydrangea serrata* Amacha), Jiaogulan, Kapor tea, Kava root, Kratom, Kuzuyu, Labrador tea, Lapacho (also known as Taheebo), Lemon Balm, Lemon and ginger tea, Lemon grass, Luo han guo, Licorice root, Lime blossom, Mint, Mountain Tea, Neem leaf, Nettle leaf, New Jersey Tea, Noni tea, Oksusu cha, Pennyroyal leaf, Pine tea, Qishr, Red clover tea, Red raspberry leaf, Roasted barley tea, Roasted wheat, Rooibos (Red Bush), Rose hip, Roselle petals (species of Hibiscus; aka Bissap, Dah, etc.), Rosemary, Sagebrush, California Sagebrush, Sage, Sakurayu, *Salvia*, Scorched rice, Skullcap, Serendib (tea), Sobacha, Spicebush (*Lindera benzoin*), Spruce tea, Staghorn sumac fruit, *Stevia*, St. John's Wort, Tea (*Camellia sinensis*), Thyme, Tulsi, Holy Basil, *Uncaria tomentosa*, commonly known as Cat's Claw, Valerian, *Verbena* (Vervains), Vetiver, Wax gourd, Wong Lo Kat, Woodruff, and/or Yarrow.

The plant, for example, can also be selected from the group consisting of culinary herbs and spices (which can be used alone or in conjunction with one of the teas or herbal tea plants) such as:

Ajwain, carom seeds (*Trachyspermum ammi*), Akudjura (*Solanum centrale*), Alexanders (*Smyrnium olusatrum*), Alkanet (*Alkanna tinctoria*), Alligator pepper, mbongo spice (mbongochobi), hepper pepper (*Aframomum danieffi, A. citratum, A. exscapum*), Allspice (*Pimenta dioica*), Angelica (*Angelica archangelica*), Anise (*Pimpinella anisum*), Aniseed myrtle (*Syzygium anisatum*), Annatto (*Bixa orellana*), Apple mint (*Mentha suaveolens*), Asafoetida (*Ferula assafoetida*), Asarabacca (*Asarum europaeum*), Avens (*Geum urbanum*), Avocado leaf (*Peresea americana*), Barberry (*Berberis vulgaris* and other *Berberis* spp.), Basil, sweet (*Ocimum basilicum*), Basil, lemon (*Ocimum*×*citriodorum*), Basil, Thai (*O. basilicum* var. *thyrsiflora*), Basil, Holy (*Ocimum tenuiflorum*), Bay leaf (*Laurus nobilis*), Bay leaf, Indian, tejpat, malabathrum, Boldo (*Peumus boldus*), Borage (*Borago officinalis*), Black cardamom (*Amomum subulatum, Amomum costatum*), Black mustard (*Brassica nigra*), Blue fenugreek, blue melilot (*Trigonella caerulea*), Brown mustard (*Brassica juncea*), Caraway (*Carum carvi*), Cardamom (*Elettaria cardamomum*), Carob (*Ceratonia siliqua*), Catnip (*Nepeta cataria*), Cassia (*Cinnamomum aromaticum*), Cayenne pepper (*Capsicum annuum*), Celery leaf (*Apium graveolens*), Celery seed (*Apium graveolens*), Chervil (*Anthriscus cerefolium*), Chicory (*Cichorium intybus*), Chili pepper (*Capsicum* spp.), Chives (*Allium schoenoprasum*), Cicely, sweet cicely (*Myrrhis odorata*), Cilantro, coriander greens, coriander herb (*Coriandrum sativum*), Cinnamon, Indonesian (*Cinnamomum burmannii, Cassia vera*), Cinnamon, Saigon or Vietnamese (*Cinnamomum loureiroi*), Cinnamon, true or Ceylon (*Cinnamomum verum, C. zeylanicum*), Cinnamon, white (*Canella winterana*), Cinnamon myrtle (*Backhousia myrtifolia*), Clary, Clary sage (*Salvia sclarea*), Clove (*Syzygium aromaticum*), Coriander seed (*Coriandrum sativum*), Costmary (*Tanacetum balsamita*), Cuban oregano (*Plectranthus amboinicus*), Cubeb pepper (*Piper cubeba*), Cudweed (*Gnaphalium* spp.), Culantro, culangot, long coriander (*Eryngium foetidum*), Cumin (*Cuminum cyminum*), Curry leaf (*Murraya koenigii*), Curry plant (*Helichrysum italicum*), Dill seed (*Anethum graveolens*), Dill herb or weed (*Anethum graveolens*), Elderflower (*Sambucus* spp.), Epazote (*Dysphania ambrosioides*), Fennel (*Foeniculum vulgare*), Fenugreek (*Trigonella foenumgraecum*), File powder, gumbo file (*Sassafras albidum*), Fingerroot, krachai, temu kuntji (*Boesenbergia rotunda*), Galangal, greater (*Alpinia galanga*), Galangal, lesser (*Alpinia officinarum*), Galingale (*Cyperus* spp.), Garlic chives (*Allium tuberosum*), Garlic (*Allium sativum*), Garlic, elephant (*Allium ampeloprasum* var. *ampeloprasum*), Ginger (*Zingiber officinale*), Ginger, torch, bunga siantan (*Etlingera elatior*) (Indonesia), Golpar, Persian hogweed (*Heracleum persicum*) (Iran), Grains of paradise (*Aframomum melegueta*), Grains of Selim, Kani pepper (*Xylopia aethiopica*), Horseradish (*Armoracia rusticana*), Houttuynia cordata (Vietnam), Huacatay, Mexican marigold, mint marigold (*Tagetes minuta*), Hyssop (*Hyssopus officinalis*), Indonesian bay leaf, daun salam (*Syzygium polyanthum*), Jasmine flowers (*Jasminum* spp.), Jimbu (*Allium hypsistum*) (Nepal), Juniper berry (*Juniperus communis*), Kaffir lime leaves, Makrud lime leaves (*Citrus hystrix*) (Southeast Asia), Kala zeera (or kala jira), black cumin (*Bunium persicum*) (South Asia), Kawakawa seeds (*Macropiper excelsum*) (New Zealand), Kencur, galangal, kentjur (*Kaempferia galanga*), Keluak, kluwak, kepayang (*Pangium edule*), Kinh gioi, Vietnamese balm (*Elsholtzia ciliata*), Kokam seed (*Garcinia indica*) (Indian confectionery), Korarima, Ethiopian cardamom, false cardamom (*Aframomum corrorima*) (Eritrea), Koseret leaves (*Lippia adoensis*) (Ethiopia), Lavender (*Lavandula* spp.), Lemon balm (*Melissa officinalis*), Lemongrass (*Cymbopogon citratus, C. flexuosus*, and other *Cymbopogon* spp.), Lemon ironbark (*Eucalyptus staigeriana*) (Australia), Lemon myrtle (*Backhousia citriodora*) (Australia), Lemon *verbena* (*Lippia citriodora*), Leptotes bicolor (Paraguay and southern Brazil), Lesser calamint (*Calamintha nepeta*), nipitella, nepitella (Italy), Licorice, liquorice (*Glycyrrhiza glabra*), Lime flower, linden flower (*Tilia* spp.), Lovage (*Levisticum offi-* cinale), Mace (*Myristica fragrans*), Mahlab, St. Lucie cherry (*Prunus mahaleb*), Marjoram (*Origanum majorana*), Marsh mallow (*Althaea officinalis*), Mastic (*Pistacia lentiscus*), Mint (*Mentha* spp.) 25 species, hundreds of varieties, Mountain horopito (*Pseudowintera colorata*) 'Pepperplant' (New Zealand), Musk mallow, abelmosk (*Abelmoschus moschatus*), Mustard, black, mustard plant, mustard seed (*Brassica nigra*), Mustard, brown, mustard plant, mustard seed (*Brassica juncea*), Mustard, white, mustard plant, mustard seed (*Sinapis alba*), Nasturtium (*Tropaeolum majus*), Nigella, kalonji, black caraway, black onion seed (*Nigella sativa*), Njangsa, djansang (*Ricinodendron heudelotii*) (West Africa), Nutmeg (*Myristica fragrans*), Neem, Olida (*Eucalyptus olida*) (Australia), Oregano (*Origanum vulgare, O. heracleoticum*, and other species), Orris root (*Iris germanica, I. florentina, I. pallida*), Pandan flower, kewra (*Pandanus odoratissimus*), Pandan leaf, screwpine (*Pandanus amaryffifolius*, Paprika (*Capsicum annuum*), Paracress (*Spilanthes acmella, Soleracea*) (Brazil), Parsley (*Petroselinum crispum*), Pepper: black, white, and green (*Piper nigrum*), Pepper, Dorrigo (*Tasmannia stipitata*) (Australia), Pepper, long (*Piper longum*), Pepper, mountain, Cornish pepper leaf (*Tasmannia lanceolata*), Peppermint (*Mentha piperata*), Peppermint gum leaf (*Eucalyptus dives*), Perilla, shiso (*Perilla* spp.), Peruvian pepper (*Schinus molle*), Pandanus amaryllifolius, Brazilian pepper or Pink pepper (*Schinus terebinthifolius*), Quassia (*Quassia amara*) (bitter spice in aperitifs and some beers and fortified wines), Ramsons, wood garlic (*Allium ursinum*), Rice paddy herb (*Limnophila aromatica*) (Vietnam), Rosemary (*Rosmarinus officinalis*), Rue (*Ruta graveolens*), Safflower (*Carthamus tinctorius*), for yellow color, Saffron (*Crocus sativus*), Sage (*Salvia officinalis*), Saigon cinnamon (*Cinnamomum loureiroi*), Salad burnet (*Sanguisorba minor*), Salep (*Orchis mascula*), Sassafras (*Sassafras albidum*), Savory, summer (*Satureja hortensis*), Savory, winter (*Satureja montana*), Silphium, silphion, laser, laserpicium, lasarpicium (Ancient Roman cuisine, Ancient Greek cuisine), Shiso (*Perilla frutescens*), Sorrel (*Rumex acetosa*), Sorrel, sheep (*Rumex acetosella*), Spearmint (*Mentha spicata*), Spikenard (*Nardostachys grandiflora* or *N. jatamansi*), Star anise (*Illicium verum*), Sumac (*Rhus coriaria*), Sweet woodruff (*Galium odoratum*), Szechuan pepper, Sichuan pepper (*Zanthoxylum piperitum*), Tarragon (*Artemisia dracunculus*), Thyme (*Thymus vulgaris*), Thyme lemon (*Thymus×citriodorus*), Turmeric (*Curcuma longa*), Vanilla (*Vanilla planifolia*), Vietnamese cinnamon (*Cinnamomum loureiroi*), Vietnamese coriander (*Persicaria odorata*), Voatsiperifery (*Piper borbonense*), Wasabi (*Wasabia japonica*), Waterpepper, smartweed (*Polygonum hydropiper*), Watercress (*Rorippa nasturtium-aquatica*), Wattleseed (from about 120 spp. of Australian *Acacia*), White mustard (*Sinapis alba*), Wild betel (*Piper sarmentosum*) (Southeast Asia), Wild thyme (*Thymus serpyllum*), Willow herb (*Epilobium parviflorum*), Winter savory (*Satureja montana*), Wintergreen (*Gaultheria procumbens*), Wood avens, herb bennet (*Geum urbanum*), Woodruff (*Galium odoratum*), Wormwood, absinthe (*Artemisia absinthium*), Yellow mustard (*Brassica hirta=Sinapis alba*), Yerba buena, any of four different species, many unrelated, Za'atar (herbs from the genera *Origanum, Calamintha, Thymus*, and/or *Satureja*), Zedoary (*Curcuma zedoaria*).

The plant can also be selected from the group consisting of medicinal plants such as:

Arai (*Euterpe oleracea*, Alfalfa (*Medicago sativa*), Arnica (*Arnica Montana*, Asthma weed (*Euphorbia hirta*), Astragalus (*Astragalus propinquus*), Barberry (*Berberis vulgaris*), Belladonna (*Atropa belladonna*, Bilberry (*Vaccinium myrtillus*), Bitter gourd (*Momordica charantia*), Bitter leaf (*Vemonia amygdalina*), Bitter orange (*Citrus×aurantium*), Black cohosh (*Actaea racemosa*), Blessed thistle (*Cnicus benedictus*), Blueberries (*genus Vaccinium*), Burdock (*Arctium lappa*), Cat's claw (*Uncaria tomentosa*), Cayenne (*Capsicum annuum*), Celery (*Apium graveolens*), Chamomille (*Matricaria recutita and Anthemis nobilis*), Chaparral (*Larrea tridentata*), Chasteberry (*Vitex agnus-castus*), Chili (*Capsicum frutescens*), Cinchona, Clove (*Syzygium aromaticum*), Coffee senna (*Cassia occidentalis*), Comfrey (*Symphytum officinale*), Cranberry (*Vaccinium macrocarpon*), Dandelion (*Taraxacum officinale*), Dong quai (*Angelica sinensis*), Elderberry (*Sambucus nigra*), Eucalyptus (*Eucalyptus globulus*), European Mistletoe (*Viscum album*), Evening primrose (*Oenothera* spp.), Fenugreek (*Trigonella foenum-graecum*), Feverfew (*Tanacetum parthenium*), Flaxseed (*Linum usitatissimum*), Garlic (*Allium sativum*), Ginger (*Zingiber officinale*), Gingko (*Gingko biloba*), Ginseng (*Panax ginseng and Panax quinquefolius*), Goldenseal (*Hydrastis canadensis*), Grape (*Vitis vinifera*), Guava (*Psidium guajava*), Hawthorn (specifically *Crataegus monogyna* and *Crataegus laevigata*), Hoodia (*Hoodia gordonii*), Horse chestnut (*Aesculus hippocastanum*), Horsetail (*Equisetum arvense*), Jamaica dogwood (*Piscidia erythrina* or *Piscidia piscipula*), Kava (*Piper methysticum*), Kha, Konjac (*Amorphophallus konjac*), Kratom (*Mitragyna speciosa*), Kanna (*Sceletium tortuosum*), Lavender (*Lavandula angustifolia*), Lemon (*Citrus limon*), Licorice root (*Glycyrrhiza glabra*), Marigold (*Calendula officinalis*), Marsh mallow (*Althaea officinalis*), Milk thistle (*Silybum marianum*), Neem (*Azadirachta indica*), Noni (*Morinda citrifolia*), Oregano (*Origanum vulgare*), Papaya (*Carica papaya*), Peppermint (*Mentha×piperita*), Purple coneflower (*Echinacea purpurea*), Passion Flower (*Passiflora*), Red clover (*Trifolium pratense*), Rosemary (*Rosmarinus officinalis*), Sage (*Salvia officinalis*), Syrian Rue (aka Harmal) (*Peganum harmala*), St. John's wort (*Hypericum perforatum*), Saw palmetto (*Serenoa repens*), Thunder God Vine (*Tripterygium wilfordii*), Thyme (*Thymus vulgaris*), Tulasi (*Ocimum tenuiflorum* or Holy Basil), Turmeric (*Curcuma longa*), Umckaloabo (*Pelargonium sidoides*), Valerian (*Valeriana officinalis*), White willow (*Salix alba*), and/or Yerba santa (*Eriodictyon crassifolium*).

As disclosed herein, mixtures of the above-mentioned culinary, herbal and/or medicinal plants are also included in the present disclosure.

In a preferred embodiment of the disclosure, the plant is tea (*Camellia sinensis*), including white tea, yellow tea, green tea, oolong tea, black tea, and/or pu-erh tea, and the like, including mixtures or blends thereof.

In one embodiment, the composition (either for making a drink or as a mixture of herbs and spices) comprises a layer of fibrous plant product, wherein the fibrous plant product comprises a blend of different plants.

In one embodiment, the composition (either for making a drink or as a mixture of herbs and spices) comprises a plant extract, wherein the plant extract comprises a blend of different plants.

In another embodiment, the composition comprises a layer of fibrous plant product and a plant extract applied thereto, wherein the fibrous plant product comprises a blend of different plants and the plant extract comprises a blend of different plants, or wherein the fibrous plant product comprises a single plant and the plant extract comprises a blend of different plants, or wherein the fibrous plant product comprises a blend of different plants and the plant extract comprises a single plant.

In another embodiment of the composition, the layer of fibrous plant product and the plant extract are from the same plant or mixture of plants or from different plants.

In one embodiment, the layer of fibrous plant product of the composition comprises at least 70% (w/w) of fibrous plant product from one plant.

In one embodiment, the plant extract comprises at least 70% (w/w) of a plant extract from one plant. In another embodiment, the composition comprises at least 70% of fibrous plant product, preferably where the at least 70% of a plant extract is from tea.

One process for producing the composition of the present disclosure will now be discussed in greater detail. In general, one method for producing the composition for making a beverage or broth includes the following steps:

a) extracting components of at least one plant with a solvent;

b) separating the soluble portion (plant extract) from the non-soluble portion (solid plant particles);

c) optionally refining the non-soluble portion;

d) preparing a sheet-like product from the non-soluble portion;

e) optionally concentrating the soluble portion;

f) applying the soluble portion of step b) or concentrated soluble portion of step e) to the sheet of step d);

g) drying the product of step f) to obtain the composition for making a beverage; and h) optionally, reducing the sheet-like material into discrete pieces.

In one embodiment of the invention, one or more plant components (plant material or plant funish) such as, for example, stems, scraps, leaves, fines, dust and/or shorts, are initially mixed with a solvent (e.g., water and/or other compounds) at elevated temperatures. For example, various solvents that are water-miscible, such as alcohols (e.g., ethanol), can be combined with water to form an aqueous solvent. The water content of the aqueous solvent can, in some instances, be greater than 50% by weight of the solvent. In one embodiment, the water content is 70%, 80%, 90% or 100%. Deionized water, distilled water or tap water may be employed. The amount of the solvent in the suspension can vary widely, but is generally added in an amount from about 75% to about 99% by weight of the suspension. However, the amount of solvent can vary with the nature of the solvent, the temperature at which the extraction is to be carried out, and the type of plant components.

After forming the solvent/plant furnish mixture, some or all of a soluble extracts fraction of the furnish mixture may be optionally separated (e.g., extracted) from the mixture. If desired, the aqueous solvent/plant furnish mixture can be agitated during extraction by stirring, shaking or otherwise mixing the mixture in order to increase the rate of extraction. Typically, extraction is carried out for about 0.5 hours to about 6 hours. Moreover, although not required, typical extraction temperatures range from about 10° C. to about 100° C.

Prior to the extraction step an optional grinding or cutting step can be used, in order to shred the plant or plant part and thus to break the plant's cell walls. Such step will increase surface exchange and improve extraction.

Once separated from the insoluble residue fraction of the plant solution, the soluble extracts fraction can optionally be concentrated using any known type of concentrator, such as a vacuum evaporator. In one embodiment, the soluble component may be highly concentrated. Moreover, the concentrated or unconcentrated soluble extracts fraction can be utilized in any manner desired. For example, the soluble extracts fraction can be utilized as a flavouring material or a portion can be added to the insoluble residue fraction.

Once extracted, the insoluble residue fraction can optionally be subjected to one or more mechanical refiners to produce a fibrous pulp. Some examples of suitable refiners can include disc refiners, conical refiners, and the like. The refined insoluble residue fraction can be utilized in any manner desired. For example, the insoluble residue fraction can be used as a flavouring material, used to produce a composition of the invention, which is herein also referred to as reconstituted plant material.

To produce a composition of the invention, the insoluble residue fraction may be transferred to a papermaking station. The papermaking station includes a forming apparatus, which may include, for example, a forming wire, gravity drain, suction drain, felt press, Yankee dryer, drum dryers, etc. In general, the insoluble residue fraction may be in the form of a pulp. In the forming apparatus, the pulp is laid onto a wire belt forming a sheet-like shape. Excess water is removed from the tobacco sheet using gravity drains, suction drains, presses, and dryers. In addition to forming a sheet on a forming fabric or instead of forming a sheet on a forming fabric, the insoluble residue fraction may be fed to an extruding device for producing a fibrous structure or network. Thereafter, if desired, a portion of the soluble extracts fraction may be reapplied to the insoluble residue fraction. When the insoluble residue fraction is recombined with the soluble extracts fraction, the resulting plant product is generally referred to as "reconstituted plant material."

Reconstituted plant material can generally be formed in a variety of ways. For instance, in one embodiment, band casting can be utilized to form the reconstituted plant material. Band casting typically employs a slurry of finely divided plant parts mixed with a binder such as gum arabic, guar gum, alginate, xanthan, cellulose and cellulose derivatives (such as carboxy methyl cellulose (CMC), hydroxypropyl methyl cellulose (HPMC)), pectines or starch that is coated onto a steel band and then dried. In one embodiment, the method is performed according to a process similar to the conventional tobacco reconstitution process, which is for example described in U.S. Pat. Nos. 3,353,541; 3,420,241; 3,386,449; 3,760,815; and 4,674,519; which are incorporated herein in their entirety by reference thereto. The method for producing the products of the invention can also be performed by a papermaking process, in order to reconstitute any plant components (such as stems, scraps, leaves, fines, dust and/or shorts) into a paper-like product. Some examples of such processes are described in U.S. Pat. Nos. 3,428,053; 3,415,253; 3,561,451; 3,467,109; 3,483,874; 3,860,012; 3,847,164; 4,182,349; 5,715,844; 5,724,998; and 5,765,570; which are also incorporated herein in their entirety by reference thereto for all purposes. For example, the formation of the products of the invention using papermaking techniques can involve the steps of mixing fruits, herbs, medicinal plants, tea, vegetables and/or spices with water, extracting the soluble ingredients therefrom, concentrating the soluble ingredients, refining the fruits, herbs, medicinal plants, tea, vegetables and/or spices, forming a web, reapplying the concentrated soluble ingredients, drying, and threshing.

With respect to the non-soluble portion (solid plant particles) used in providing the non-impregnated fiber web of the invention, ie. the sheet-like product in step d), the plant is not tobacco, wood pulp, cotton, textiles, jute flax, Indian hemp, hemp, hoopvine, kenaf, nettles, ramie, aback bamboo fiber, banana (especially banana bark), bowstring hemp, coir (fiber from the coconut shell), esparto, henequen, kapok, milkweed, *papaya*, phormium ("New Zealand Flax"), sisal, raffia, bagasse, pina, aibika or *yucca*. However, a mixture of a plant mentioned herin in connection with the present invention with any of the aforementioned plants may be utilized. Further to the foregoing listed materials also others materials can be added to improve product physical characteristics, for example cellulose derivatives such as methylcellulose, carboxymethyl cellulose (CMC), hydroxypropyl methyl cellulose (HPMC), starch and starch derivatives such as oxidatively degraded starch, polysaccharides (and their derivatives) such as pectines, gelatins, guar gum, agar, alginates, carrageenans, or synthetic fibers such as the ones made of vinyl chloride or vinyl acetate, polyethylene, polypropylene, polyesters.

Once extracted, the insoluble, solids portion can optionally be subjected to one or more mechanical refiners to produce a fibrous pulp. Some examples of suitable refiners can include disc refiners, conical refiners, and the like, well known to a skilled person. The pulp from the refiner can then be transferred to a papermaking station (not shown) that includes a forming apparatus, which may include, for example, a forming wire, gravity drain, suction drain, felt press, Yankee dryer, drum dryers, etc. In such a forming apparatus, the pulp is laid onto a wire belt forming a sheet-like shape and excess water is removed by the gravity drain and suction drain and presses. Once separated from the insoluble portion of the plant solution (plant extract), the soluble portion can optionally be concentrated using any known type of concentrator, such as a vacuum evaporator.

In some embodiments of the invention, a wet strength agent may be added to the fibrous portion in order to reduce potential degradation of the reconstituted material when it is brought into contact with a liquid (e.g. water), such as upon infusion in water. Any suitable wet strength agent preferably selected for food applications may be used such as polyamide-epichlorohydrin resins, polyamine-epichlorohydrin resins, poly(aminoamide)-epichlorohydrin resins, urea-formaldehyde resins; melamine-formaldehyde resins; alkyl ketene dimer; alkyl succinic anhydride; polyvinylamines; oxidized polysaccharides (such as oxidatively degraded starch); glyoxalated polyacrylamide resins; polyimines such as polyethyleneimine. Wet strength agents are well known to the skilled person and described in Ingredients Standards, such as BFR (Bundesinstitut für Risikobewertung) XXXVI and BFR XXXVI/1 or FDA (Food & Drug Administration) 21 CFR 176.170, FDA 21 CFR 176.110, FDA 21 CFR 176.120, FDA 21 CFR 176.1180. The wet strength agent is for example used in an amount of about 0.1% w/w to about 20% w/w, preferably of about 1 w/w to about 10% w/w, more preferably of about 5% w/w. The wet strength agent is preferably added to the fibrous portion when or before making the sheet-like product (see step d) above).

In one embodiment, the water used for extraction is hot water, preferably of about 30 to 100° C., 40 to 90° C., or 50- to 80° C., or more preferably of about 70° C.

In one embodiment, the coating ratio of solubles portion onto the fiber web is about 5% to 80% (w/w), 10 to 70% (w/w), or more preferably between 20 and 50% (w/w). In some embodiments, the coating ratio or soluble portion that is added back to the base web (fiber web) is similar to the portion of soluble material contained in and extracted from the original plant (so called "standard level").

In one embodiment, the basis weight of the final product is about 20 to about 200 g/m² (dry basis), more preferably about 90 to about 120 g/m².

The extraction time depends on the fruits, herbs, medicinal plants, tea, vegetables and/or spices subjected to the extraction process. In one embodiment of the invention, the extraction time is about 15 to 60 minutes, preferably 45 minutes.

In one embodiment, the extracting step is performed using components of a blend of plants, in another embodiment, extracting step is performed using components of a single plant.

Extraction may also be performed by means other than using hot water, namely by extraction with supercritical gases, such as carbon dioxide, or by using, for example, ethanol, hexane, acetone, R134a (1,1,1,2-tetrafluoroethane), carbon dioxide and hydrofluorocarbons. In one embodiment, the extraction can be carried out by using at least one solvent at room temperature and under atmospheric pressure. Extraction may also be performed by using a mixture of different solvents. In another embodiment, extraction may be performed using at least one solvent, such as for example R134a or carbon dioxide, at different temperatures and at different pressures and different states (liquid or gaseous). For example, extraction may be performed using solvents in a liquid state (such as solvent that are volatile or non-volatile at room temperature), in a subcritical state (such as water at a temperature above 100° C. and a pressure above 1 bar), or in a supercritical state (such as carbon dioxide at a temperature above 31° C. and a pressure above 73 bar).

Certain plants may require specific extraction conditions (time, temperature, solid/liquid ratio) due to the ingredients contained therein, which may be temperature sensitive or must not be subjected to certain extraction conditions. For example, extraction of lycopene from tomatoes we must be performed by using specific enzymes to liberate the product from tomatoes cells. In connection with the present invention, processing aids maybe used to improve extraction, such as pH modifiers (such as, for example, NaOH or organic acids), microwaves, pressure, ultrasound, enzymes such as for example proteases, amylases, cellulases, and/or pectinases. Whenever reference is made herein to "extraction", the term includes the aforementioned alternative extraction means. The extraction used in connection with the present invention can be performed in a continuous or discontinuous matter. The extraction conditions are well known to the skilled artisan and described in standard text books, such as Handbook of Separation Techniques for Chemical Engineers, Third Edition (March 1997), Philip A. Schweitzer, McGraw-Hill Inc.

In one embodiment, the extraction and/or pressing may be performed using at least a portion of the plant material, fresh, frozen or dried, or selected from roots, bark, seeds, stems, leaves, flowers and fruit.

Separation of the soluble portion (plant extract) from the non-soluble portion (solid plant particles) can be performed by separating the liquid phase from the solid phase, such as by filtration, with or without pressure, by centrifugation or other methods commonly used in the laboratory and well-known to the skilled person.

In a preferred embodiment of the invention, the plant used in the method of the invention is tea (*Camellia sinensis*), and the extraction is performed for about 45 minutes with water at about 70° C.

In one embodiment of the method where a mixture or blend of plants is used, the non-soluble portion of the plant is mixed with the non-soluble portion of at least one further plant prior to preparing the sheet.

Certain embodiments use the soluble portion of step b) or concentrated soluble portion of step e), which is mixed with the soluble portion or concentrated soluble portion of at least one further plant prior to applying the soluble portion or concentrated soluble portion to the sheet.

For certain applications it is desirable to adjust the composition by adding or removing ingredients or components to or from the plant extract and/or the non-soluble plant particles prior to producing the final product of the invention. Such adjustment may be performed to modify/improve chemical, physical and/or sensory characteristics of the finished product. The present disclosure thus encompasses methods, further comprising the step of adding or removing ingredients from the soluble portion (plant extract) and/or from the non-soluble portion (solid plant particles) prior to applying the soluble portion of step b) or concentrated soluble portion of step e) to the sheet of step d).

In some embodiments, the sheet or sheet-like product which is obtained in step g) is a web or fiber-web. In accordance with the present disclosure, the sheet-like product or web may be used in different sizes and shapes. In some cases, the composition of step g) is further cut, broken, shredded, stamped, fibrillated, or the like into small regularly or irregularly shaped forms. The composition can be formed into any desired shapes, dimensions and formats, such as leaves (or leaf-like shapes), sticks or bands. In addition to cutting or breaking the sheet or fibrous web to a desired size and/or shape or forming the same into to a desired size and/or shape, it may be dried to the desired final moisture content.

In accordance with the present disclosure, the plant is selected from the group consisting of fruits, herbs, medicinal plants, tea, vegetables and spices, including mixtures thereof, such as mixtures of herbs and vegetables. In one embodiment, the fruits, herbs, medicinal plants, tea, vegetables and spices are for example selected from *artemisia*, balm, basil, chamomile, chive, cloves, coffee, coriander, dill, garlic, ginger, *ginseng, gingko*, jasmine, lavender, mint, orange blossom, oregano, persil, rooibos, *rosa centifolia*, rosemary, thyme, turmeric, sage, pepper, chili pepper, *stevia rebaudiana*, tarragon, white tea, yellow tea, green tea, oolong tea, black tea, pu-erh tea, *vanilla*, red or green vine, violet and/or willow.

In some embodiments, the plant is selected from the group consisting of teas and herbal teas as described in detail above.

As disclosed herein, mixtures of culinary, herbal and/or medicinal plants may also be used.

In a preferred embodiment, the plant is tea (*Camellia sinensis*), including white tea, yellow tea, green tea, oolong tea, black tea, and/or pu-erh tea, and the like, including mixtures or blends thereof.

In a further embodiment, the invention relates to a fiber-web comprising from about 5% to about 100% (w/w)), preferably at least 10%, at least 20%, at least 30%, at least 40%, at least 50%, at least 60%, at least 70%, at least 80%, at least 90%, or 100%, fibers of fruits, herbs, medicinal plants, tea, vegetables and/or spices. In one embodiment, the fiber-web further comprises cellulosic and/or synthetic fibers, and fibers of fruits, herbs, medicinal plants, tea, vegetables and/or spices in a ratio of for example: 40/60 (w/w), 60/40 (w/w) or 20/80 (w/w).

The present disclosure also includes the use of the composition for making a beverage (drink, tea etc.), or broth, or for culinary use or use in cooking, respectively, i.e. as a herb and spice mixture such as a bouquet garni instead of a conventional bouquet garni. Specifically, the present disclosure includes the use of the composition of the invention for as a drink (beverage), as a food or food product, for culinary or cooking purposes, or for medicinal or aromatic applications and the like.

Also included is a beverage obtainable by contacting water with the composition.

In some embodiments, the fiber-web further comprises a coating or impregnation with soluble portion (plant extract) of fruits, herbs, medicinal plants, or tea.

The coating or impregnation is obtained by various methods known to the skilled person, such as applying to or treating the fiber-web or sheet-like structure with a plant extract, such as in a bath or by special application means, such as sprayers. In addition, various other ingredients, such as flavor or color treatments, can also be applied to the web. If applied with the soluble portion and/or other ingredients, the fibrous sheet material can, in some embodiments, then be dried using, for example, a tunnel dryer, to provide a sheet having a typical moisture content of less than 20% by weight, and particularly from about 9% to about 14% by weight.

The present disclosure thus also relates to an impregnated or coated fiber-web, obtainable by the method.

The products of the present disclosure can enable a more efficient infusion (100% solubles are extracted from the plant) in the sense that more solubles can be released than natural plant ingredients for a given weight of material. The products also provide a faster infusion (than with a conventional infusion made from the vegetal material in its natural non converted form). Specifically, the compositions of the invention have improved efficiency in boiling water or in non-heated water or water at room temperature.

The process for making the compositions also allows for specifically adjusting the final composition of the products, such as to remove from the soluble or the non-soluble portion(s) for example foreign matters, components altering taste and/or odor, or caffeine, nicotine, pesticides, aluminum, heavy metals, mycotoxins, toxicants and allergenic molecules such as coumarin, farnesol, geraniol, limonene, linalol, safrole, methyleugenol, or by adding to the soluble or the non-soluble portion(s) for example desirable additives, such as sweeteners, sugars, flavors, casings, vitamins, colorants, minerals, taste enhancers.

In another embodiment, the soluble portion in the reconstituted material of the invention can be precisely adjusted (decreased as compared to standard level, at standard level, or increased as compared to standard level). A key benefit is that the level of ingredients in the reconstituted material can be precisely increased to a level higher than in the original natural form, thus allowing for more concentrated (more intense) drinks, teas or broths. The adjustment of ingredients can also guarantee a consistent, standardized level of delivered ingredients to compensate natural variations of active ingredients in plants.

The method of producing the composition also allows for reduction of undesired compounds from the material, such as to selectively remove undesired components (such as, for example but not limited to, natural ingredients, caffeine, nicotine, aluminum, heavy metals, pesticides, impurities or the like). For example, it is possible to remove components from either the soluble portion (plant extract) or from the non-soluble portion (solid plant particles) or both by liquid-liquid extraction, physical adsorption, centrifugation, chromatography, crystallization, decantation, by use of a demister, drying, distillation, electrophoresis, elutriation, evaporation, solid phase or liquid-liquid extraction, flotation, flocculation, filtration (for example using membranes), vapor-liquid separation, and/or sublimation and other means well known to the skilled person, preferably before applying the plant extract to the base web.

In connection with adding ingredients, extracts of different sources and origins, flavors, coloring agents or the like may be used, such as clorophyll, anthocyans, caramel, caroteinoids. For example, when using tea or herbs it is possible to include L-menthol at various quantities (such as 6% or 15%) in the finished product. Products so obtained have a distinctive taste and aroma of menthol. In one embodiment, eugenol, thymol or plant extracts/concentrates can be added to the reconstituted bouquet garni of the invention.

The composition may contain a blend of various plants and herbs. In one example, instead of using single plants, such as tea or mint leaves, tea may be replaced by a mixture of, for example, 50% tea and 50% mint leaves (w/w); 50% verbena and 50% mint (w/w); 30% cinnamon and 30% tea and 10% licorice and 10% chamomile and 10% red vine and 10% roobois (w/w); and many other combinations.

The combination of different plant materials through the reconstitution process into a single fiber web impregnated with extracts from different plants (the same plant or blends) offers new taste experiences and additive or synergistic effects. For example, it is known that combinations of certain plant extracts or combinations of certain plant ingredients have additive or synergistic effects, such as, for example, a mixture of hops and valerian extracts for use in treating insomnia and vigilance (Blumenthal and al., J. Herbal Medicine, expanded Commission E monographs, American Botanical Council, Austin, 2000, 394-400), or mixtures of oregano and cranberry extracts for use in treating *H. pylori* infections (Lin et al., Appl. Environ. Microbiol. December 2005, vol. 71, no. 12, 8558-8564), or different mixtures of extracts of *S. baicalensis, D. morifolium, G. uralensis* and *R. rubescens* tested for their additive or synergistic effect in prostate cancer cell lines (Adams et al., Evid Based Complement Alternat Med. 2006 March; 3(1): 117-124).

In the context of the present invention, the reconstituted plant material or product of the invention may be used to blend a single plant (or a mixture of different plants) together with natural materials, such as, for example, reconstituted black tea with natural tea material or reconstituted mint (*Mentha* spp.) with natural green tea material, in order to improve the quality (such as the chemical constitution, the consistency or sensory profile and characteristics) of the product or blend.

It has been found that some beverages are particularly less astringent and bitter when prepared from the reconstituted plant material or product of the invention as compared to original material from which the reconstituted plant material or product of the invention was prepared. This is, for example, the case for green tea, which is less astringent and bitter when made from a reconstituted green tea product according to the invention as compared to a conventional infusion of green tea.

The production method also provides for reducing microbiological load of the final products because of the high temperatures during the papermaking process.

In addition to a composition as described above, the present disclosure is also directed to a product for producing a beverage or broth wherein the composition as described above is contained within a porous container that allows a liquid, such as water, to contact the composition to allow the liquid to be infused with flavorants contained in the composition. The container may comprise a pouch or bag, may contain one or more gussets, and can have any suitable shape. In one embodiment, the container may include a tether that allows the user to dip the container into a liquid such as water.

Because the particle size distribution of the composition can be controlled, the porous material used to form the container can have a relatively high porosity in comparison to many tea bag materials used in the past. In one embodiment, the container is made from a high porosity paper or from a synthetic material, such as nylon. When forming a single serving drink or beverage, the container may contain the composition of the present disclosure in an amount greater than about 1 gram, such as greater than about 2 grams, such as greater than about 3 grams, such as greater than about 4 grams. The container may contain the composition in an amount generally less than about 20 grams, such as less than about 18 grams, such as less than about 15 grams, such as less than about 13 grams, such as less than about 10 grams, such as less than about 8 grams, such as less than about 7 grams, such as less than about 6 grams, such as less than about 5 grams, such as less than about 4 grams, such as even less than about 3 grams in certain applications.

The following examples further describe and demonstrate embodiments that are within the scope of the present invention. The examples are given solely for the purpose of illustration, and are not to be construed as limitations of the present invention since many variations thereof are possible without departing from its spirit and scope.

Example No. 1

A reconstituted product was made according to the following method: Rooibos (*Aspalathus linearis*) blend from commercial pyramid bags obtained from Les saveurs de Ceylan was removed from its packaging. The blend contained Rooibos material at various particle size (leaves, fannings, and dust). The blend was initially heated at 85° C. for 20 minutes with a Rooibos/water ratio of 1 to 5 by weight. This was followed by an extraction step in a hydraulic press to separate the aqueous portion from the Rooibos fiber portion. The recovered Rooibos fiber portion was again heated at 85° C. for 10 minutes with a Rooibos/water ratio of 1 to 5 by weight. After an additional extraction (by pressing), the fibrous portion was then refined in a Valley beater at 1.4% consistency for 10 minutes. After refining, the fibrous portion was used to make hand sheets. The aqueous portion was concentrated in an evaporator to a solid concentration of 50% and then coated on the hand sheet on a manual size-press. In this example, the product was produced at 22% extract content, which is the soluble content of the starting material of the experiment. The coated hand sheets were dried on a plate dryer.

The reconstituted Rooibos Tea paper was cut into regular strands of 0.8 mm by 10 mm.

Visual observation shows higher portion of long strands/less dust for reconstituted rooibos compared to the original material.

2.84 g of Rooibos and equal quantity of reconstituted Rooibos Tea paper were filled into a burette in order to determine the filling power of each. No pressing was applied onto the tea material in the burettes.

The results are shown in FIG. 1. As shown, the filling power of the composition made according to the present disclosure is approximately four times higher than the natural Rooibos blend.

Figure 2:
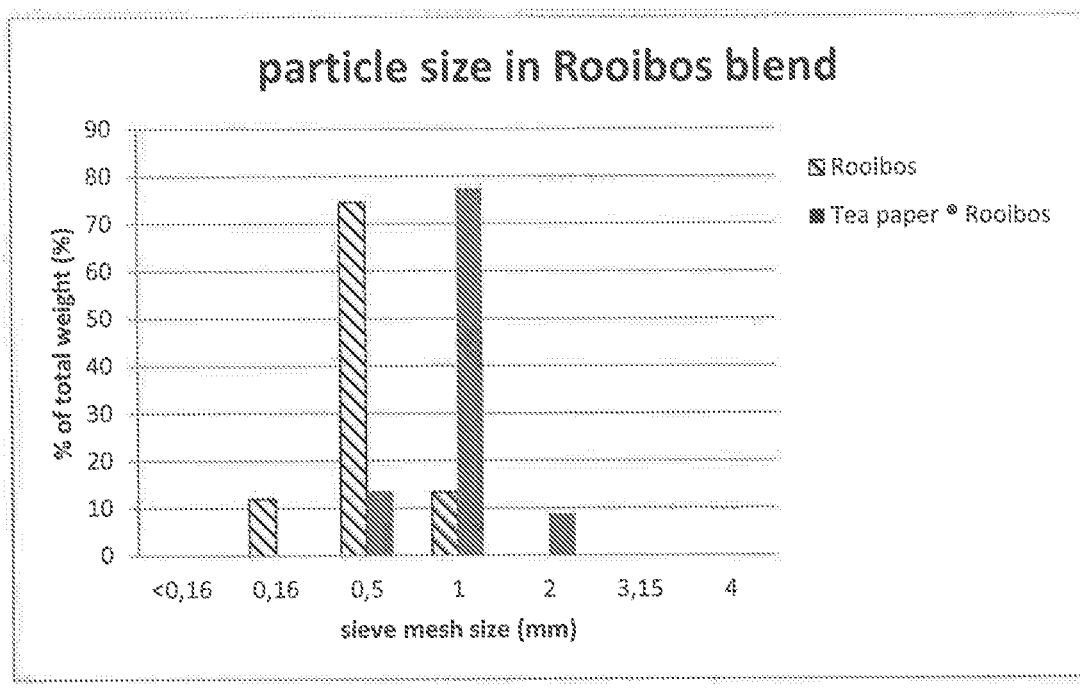

Also, it was observed that the quantity of small particles in reconstituted Rooibos blend is very limited. No dust goes through the tea bag when it is manipulated. In order to confirm this observation, the sieve test as described above was applied to natural Rooibos and reconstituted Rooibos blends. Sieving was carried out in a RETSCH sieve shaker AS200 with sieves of 4 mm, 3.15 mm, 2 mm, 1 mm, 0.5 mm and 0.16 mm square mesh. The particles were separated according to their sizes and the results are expressed in percentage of particles presence in the blend. The results are illustrated in FIG. 2.

The results show particle sizes ranging from 0.16 mm (dust) to 1 mm for natural Rooibos. 87% of the Rooibos blend went through a sieve mesh size of 1 mm (which corresponds to dust and little particles) whereas the portion of larger leaves (above 1 mm sieve mesh size) is only 13%.

The results for reconstituted Rooibos showed completely opposite conclusions where only 14% of material went through the sieve mesh size of 1 mm whereas 86% of the remaining material was above 1 mm sieve mesh size (larger strands).

This demonstrates that the average particle size of reconstituted rooibos is significantly higher that original material, offering larger pieces of product (more filling power) and less dust (less siftings).

Example No. 2

A green tea product was made according to the following method: a green tea (Sencha from China) was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After an additional extraction (by pressing), the fibrous portion was then refined in a Valley beater at 1.4% consistency for 10 minutes. After refining, the fibrous portion was used to make hand sheets. The aqueous portion was concentrated in an evaporator to a solid concentration of 50% and then coated on a hand sheet on a manual size-press. In this example, the product was produced at 36% extract content, which is the soluble content of the starting material of the experiment. The coated hand sheets were dried on a plate dryer.

The reconstituted Green Tea paper made according to the present disclosure was cut into regular strands of 0.8 mm by 10 mm.

2 g of green tea and equal quantity of reconstituted green Tea paper were filled into a burette in order to determine the filling power of each. No pressing was performed on tea material into the burettes. The result is shown in FIG. 3.

Figure 3:
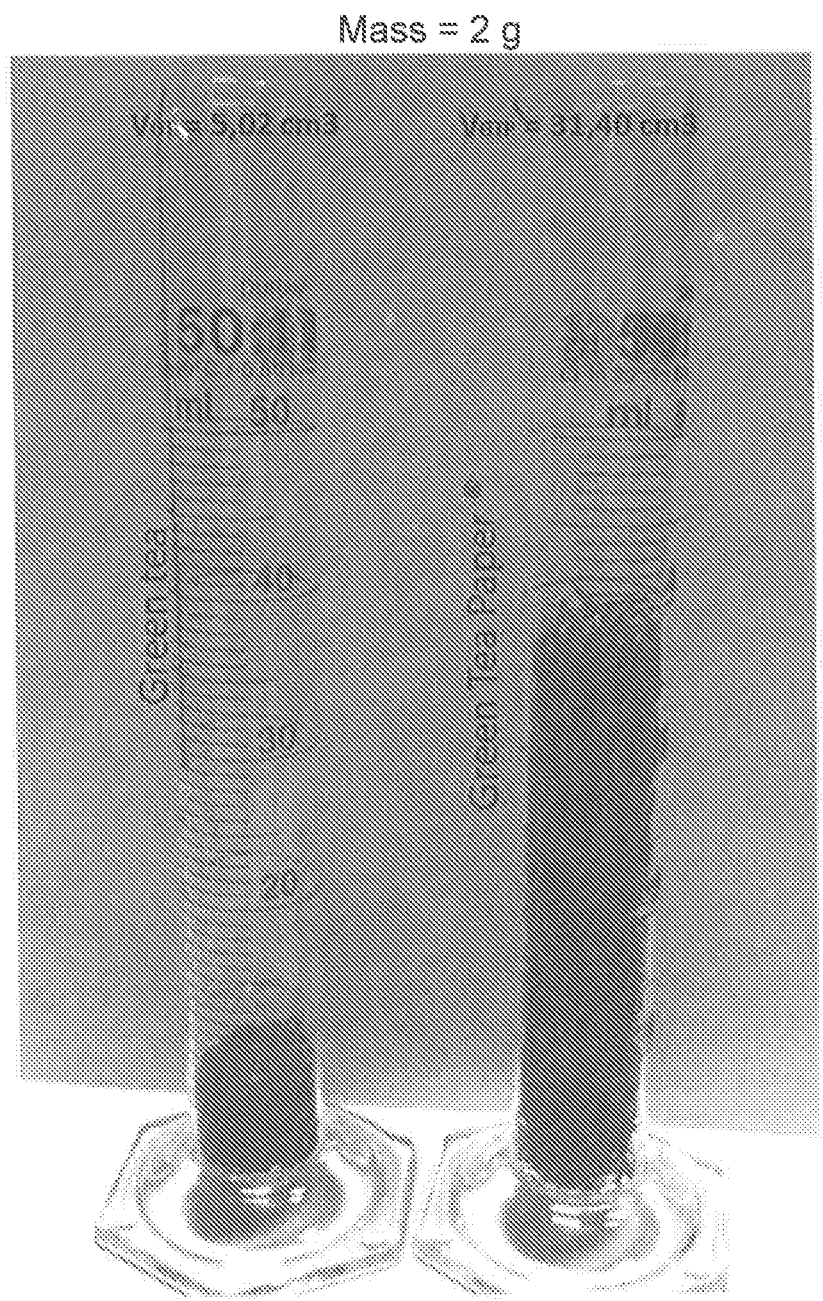

As it can be seen from FIG. 3, the filling power of reconstituted green tea is significantly higher than natural green tea. More precisely, the filling power of reconstituted green tea is about 6 times higher than natural green tea.

Figure 4:
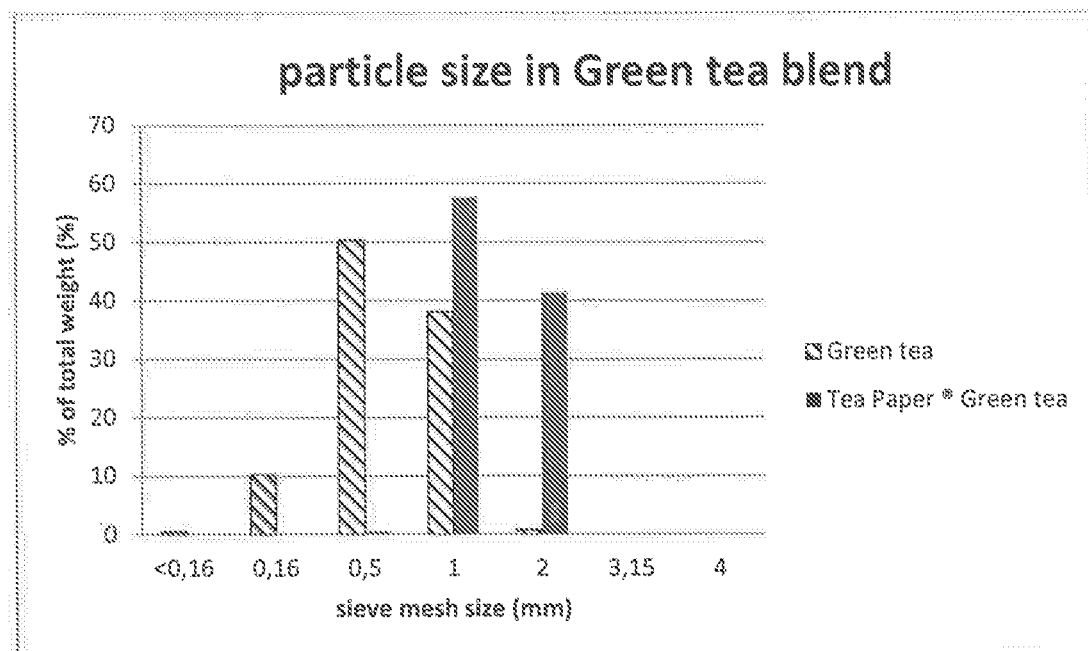

Also, it was observed that the quantity of small particles in reconstituted green tea blend is very limited. No dust goes through green tea bag when it is manipulated. In order to confirm this observation, the sieve test was applied to natural green tea and reconstituted green tea blends. Sieving is carried out in a RETSCH sieve shaker AS200 with sieves of 4 mm, 3.15 mm, 2 mm, 1 mm, 0.5 mm and 0.16 mm square mesh. The particles were separated according to their sizes and the results are expressed in percentage of particles presence in the blend and shown in FIG. 4.

The results show particle sizes ranging from 0.16 mm (dust) to 1 mm for natural green tea. 62% of the green tea blend went through a sieve mesh size of 1 mm (which corresponds to dust and little particles) whereas the portion of larger leaves (above 1 mm sieve mesh size) is only 38%.

The results for reconstituted green tea showed completely opposite conclusions where only 0.68% of the material went through the sieve mesh size of 1 mm whereas more than 99% of the remaining material was above 1 mm sieve mesh size (larger strands).

Example No. 3

A black tea product was made according to the following method: A black tea was initially heated at 85° C. for 20 minutes with a tea/water ratio of 1 to 5 by weight. This was followed by an extraction step in a hydraulic press to separate the aqueous portion from the tea fiber portion. The recovered tea fiber portion was again heated at 85° C. for 10 minutes with a tea/water ratio of 1 to 5 by weight. After refining, the fibrous portion was used to make hand sheets. The aqueous portion was concentrated in an evaporator to a solid concentration of 50% and then coated on a hand sheet on a manual size-press. The soluble level is typically between 27 and 37% in dry finished product. In this example, soluble level of the reconstituted tea was approx. 27%, which is the soluble content of conventional tea used as the starting material of the experiment. The coated hand sheets were dried on a plate dryer.

The reconstituted Black Tea paper was cut into regular strands of 0.8 mm by 10 mm. In this example, the reconstituted sheet formed from the black tea blend was cut so as to appear similar to a natural black tea blend.

2.5 g of black tea and equal quantity of reconstituted black Tea paper were filled into a burette in order to determine the filling power of each. No pressing was performed on tea material into the burettes. The results are shown in FIG. 5.

Figure 5:
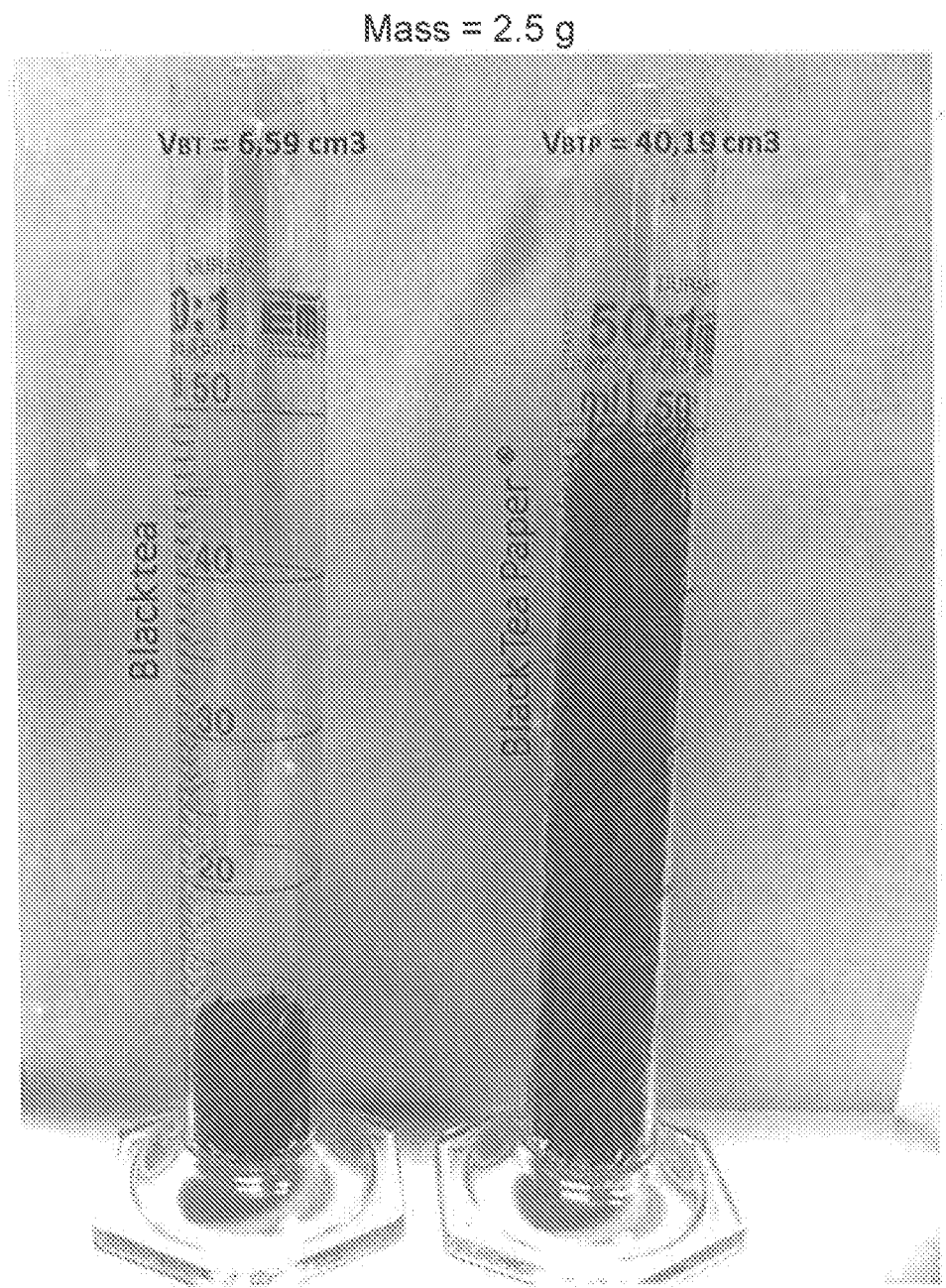

As it can be seen from FIG. 5, the filling power of reconstituted black tea is significantly higher than natural black tea. The filling power of reconstituted black tea was about 5.5 times higher than natural black tea.

Figure 6:
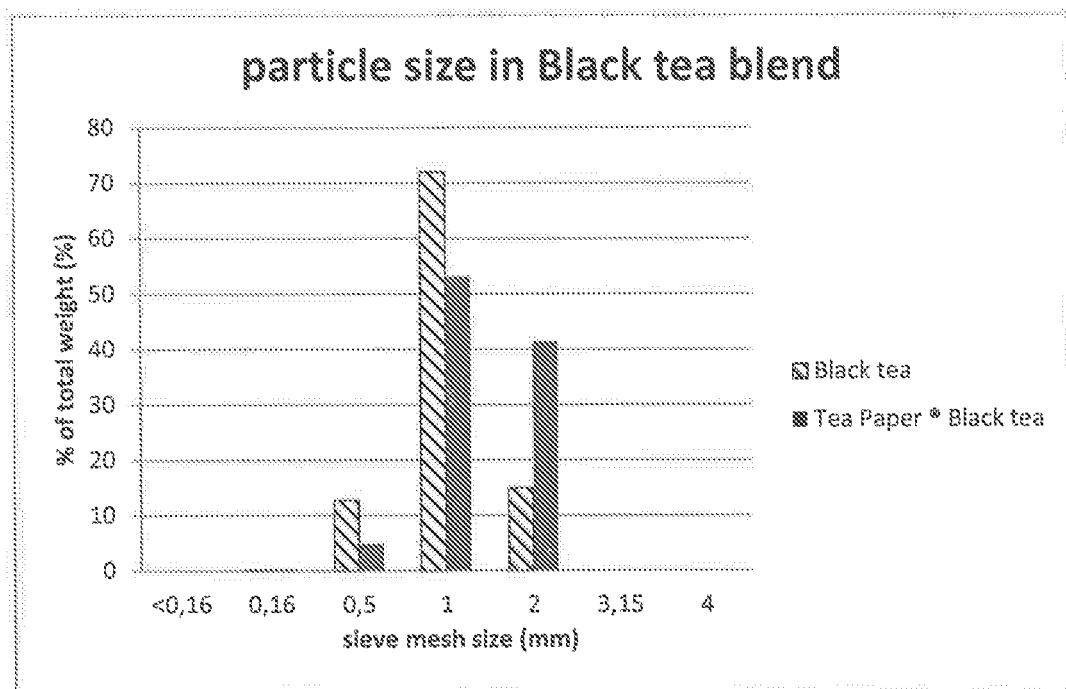
Figure 7:
FIG. 7 is a perspective view of one embodiment of a composition made in accordance with the present disclosure.

Also, it was observed that the quantity of small particles in reconstituted black tea blend is very limited. No dust goes through black tea bag when it is manipulated. In order to confirm this observation, the sieve test was applied to natural black tea and reconstituted black tea blends. Sieving is carried out in a RETSCH sieve shaker AS200 with sieves of 4 mm, 3.15 mm, 2 mm, 1 mm, 0.5 mm and 0.16 mm square mesh. The particles were separated according to their sizes and the results are expressed in percentage of particles presence in the blend. The results are shown in FIG. 6.

The results show particle size ranging from 0.16 mm (dust) to 2 mm for natural black tea. 13% of black tea blend went through a sieve mesh size of 1 mm (which corresponds to dust and little particles) whereas the portion of larger leaves (above 1 mm sieve mesh size) is about 87%.

The results for reconstituted black tea showed different distribution where only 5% of material went through the sieve mesh size of 1 mm whereas more than 95% of the remaining material was above 1 mm sieve mesh size (large strands). Moreover, more than 40% of the reconstituted black tea pieces were above 2 mm mesh size compared to 15% with natural black tea. It should be understood that the above results are when the reconstituted black tea sheet was shredded extensively to represent the black tea blend. The particle size distribution, however, may be controlled to produce less smaller sized particles by altering the manner in which the discrete pieces are formed.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A composition configured to produce a beverage or broth by soaking the composition in a liquid, the composition comprising:
    a fibrous structured matrix material formed from insoluble residue of plant materials contained in a porous container, and
    wherein the fibrous structured matrix material has been treated with a plant extract, and
    the plant material comprising materials obtained from a tea plant, an herbal tea plant, a fruit, a vegetable, a spice, or mixtures thereof, the composition being in the form of discrete pieces of the fibrous structured matrix material, the discrete pieces have a particle size distribution such that when the composition is subjected to a sieve test using a RETSCH sieve shaker AS200, less than about 25% of the pieces pass through a sieve having a square mesh size of 1 mm, less than about 1% of the pieces pass through a sieve having a square mesh size of 0.5 mm, and wherein greater than about 50% of the pieces fail to pass through a sieve having a square mesh size of 2 mm, wherein the composition has a bulk density of less than about 0.2 g/cm$^3$.

2. The composition as defined in claim 1, wherein the plant material contained in the composition comprise materials obtained from a tea plant and wherein less than 10% of the pieces pass through a sieve having a square mesh size of 1 mm and wherein greater than about 60% of the pieces fail to pass through a sieve having a square mesh size of 2 mm.

3. The composition as defined in claim 1, wherein the fibrous structured matrix material is formed from insoluble residue of plant materials comprising a black tea blend, white tea blend, yellow tea blend, oolong tea blend, pu-erh tea blend, or mixtures thereof.

4. The composition as defined in claim 1, wherein the fibrous structured matrix material is formed from insoluble residue of plant materials comprising a green tea blend.

5. The composition as defined in claim 1, wherein the fibrous structured matrix material is formed from insoluble residue of plant materials comprising a rooibos tea blend.

6. The composition as defined in claim 1, wherein the discrete pieces have a particle size distribution such that less than about 0.8% of the pieces pass through a sieve having a square mesh size of 0.5 mm.

7. The composition as defined in claim 4, wherein the discrete pieces have a particle size distribution such that less than about 5% of the pieces pass through a sieve having a square mesh size of 1 mm.

8. The composition according to claim 1, wherein the fibrous structured matrix material formed from insoluble residue of plant materials comprises a blend of different plants.

9. The composition as defined in claim 1, wherein the fibrous structured matrix material formed from insoluble residue of plant materials and the plant extract are obtained from at least one common plant.

10. The composition as defined in claim 1, wherein the fibrous structured matrix material formed from insoluble residue of plant materials comprises at least 70% of plant materials obtained from one plant.

11. The composition as defined in claim 1, wherein the plant extract comprises at least 70% of a plant extract obtained from one plant.

12. The composition as defined in claim 1, wherein at least about 70% of the plant materials used to form the structured matrix material are obtained from a tea plant or an herbal tea plant.

13. The composition as defined in claim 1, wherein at least about 70% of the plant extract is obtained from a tea plant or an herbal tea plant.

14. The composition as defined in claim 1, wherein the composition comprises pieces obtained from the structured matrix material combined with pieces of a natural tea blend or a natural herbal tea blend.

15. The composition as defined in claim 14, wherein from about 20% to about 98% of the pieces contained in the composition are produced from the fibrous structured matrix material formed from insoluble residue of the plant materials.

16. The composition as defined in claim 1, wherein the pieces contained in the composition comprise shreds obtained from the fibrous structured matrix material formed from insoluble residue of the plant materials.

17. The composition as defined in claim 1, wherein the pieces contained in the composition are in the shape of a figure.

18. The composition as defined in claim 1, wherein more than 50% of the discrete pieces have a length or largest dimension of from about 2 mm to about 10 mm.

19. A composition configured to produce a beverage or broth by soaking the composition in a liquid, the composition comprising:
    a fibrous structured matrix material formed from insoluble residue of plant materials contained in a porous container, and
    wherein the fibrous structured matrix material has been treated with a plant extract, and
    the plant material comprising materials obtained from a tea plant, an herbal tea plant, a fruit, a vegetable, a spice, or mixtures thereof, the composition being in the form of discrete pieces of the fibrous structured matrix material, the discrete pieces have a particle size distribution such that when the composition is subjected to a sieve test using a RETSCH sieve shaker AS200, less than about 25% of the pieces pass through a sieve having a square mesh size of 1 mm, less than about 1% of the pieces pass through a sieve having a square mesh size of 0.5 mm, and wherein greater than about 50% of the pieces have a length or largest dimension of greater than about 2.5 mm and fail to pass through a sieve having a square mesh size of 2 mm.

* * * * *